(12) United States Patent
Sinha et al.

(10) Patent No.: US 10,137,479 B2
(45) Date of Patent: Nov. 27, 2018

(54) TEMPORAL MULTIPLEXED EXCITATION FOR MINIATURIZED, PLANAR FLUORESCENCE ACTIVATED CELL SORTING

(71) Applicant: Verily Life Sciences LLC, Mountain View, CA (US)

(72) Inventors: Supriyo Sinha, Menlo Park, CA (US); Brian Rabkin, Redwood City, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 15/613,614

(22) Filed: Jun. 5, 2017

(65) Prior Publication Data

US 2017/0348735 A1 Dec. 7, 2017

Related U.S. Application Data

(60) Provisional application No. 62/346,206, filed on Jun. 6, 2016.

(51) Int. Cl.
*G01N 15/14* (2006.01)
*B07C 5/34* (2006.01)
(Continued)

(52) U.S. Cl.
CPC .......... *B07C 5/3412* (2013.01); *B01L 3/5027* (2013.01); *B01L 3/502761* (2013.01);
(Continued)

(58) Field of Classification Search
CPC ........... G01N 15/1404; G01N 15/1427; G01N 15/1434; G01N 15/1459; G01N 15/1484
See application file for complete search history.

(56) References Cited

U.S. PATENT DOCUMENTS 9,645,010 B2    5/2017 Lo et al.
2011/0085166 A1*  4/2011 Ou-Yang ........... B01L 3/502761
                                                      356/338

(Continued)

OTHER PUBLICATIONS

International Search Report and Written Opinion of International Application No. PCT/US2017/035887, dated Sep. 12, 2017.

(Continued)

*Primary Examiner* — Michael P Stafira
(74) *Attorney, Agent, or Firm* — McDonnell Boehnen Hulbert & Berghoff LLP (57) ABSTRACT

A system for fluorescence activated cell sorting includes at least two excitation lasers and an objective that directs light from the at least two excitation lasers to a common point in an interrogation region of a fluidic channel. The fluidic channel directs a flow of a plurality of fluorescently labeled particles through the interrogation region. At least one modulator temporally multiplexes light from the at least two excitation lasers such that pulses of light from different lasers intersect the common point at different times. The system further includes at least one detector and at least one optical element that directs light emitted from the particles and transmitted through the objective to the at least one detector. The system may further include optics for generating and detecting side and forward scattered light. Methods for operating example systems to collect fluorescent, side scattered and forward scattered light are also described herein.

20 Claims, 4 Drawing Sheets

(51) Int. Cl.
  *B01L 3/00*   (2006.01)
  *B82Y 10/00*  (2011.01)
  *B82Y 25/00*  (2011.01)
  *B82Y 30/00*  (2011.01)
  *G06K 19/06*  (2006.01)
  *G01N 15/10*  (2006.01)

(52) U.S. Cl.
  CPC .............. *B82Y 10/00* (2013.01); *B82Y 25/00* (2013.01); *B82Y 30/00* (2013.01); *G01N 15/1404* (2013.01); *G01N 15/1427* (2013.01); *G01N 15/1434* (2013.01); *G01N 15/1459* (2013.01); *G06K 19/06187* (2013.01); *B01J 2219/00509* (2013.01); *B01J 2219/00563* (2013.01); *B01L 3/54* (2013.01); *G01N 15/1484* (2013.01); *G01N 2015/1006* (2013.01); *G01N 2015/1438* (2013.01)

(56) References Cited

U.S. PATENT DOCUMENTS

| | | | |
|---|---|---|---|
| 2013/0200277 A1 | 8/2013 | Li et al. | |
| 2014/0158913 A1* | 6/2014 | Tanase | G01N 21/6428 250/459.1 |

OTHER PUBLICATIONS

Kate Yandell, "Sorting Made Simpler," The Scientist, Dec. 2104, pp. 63-66.
"NanoCellect Launched WOLF Cell Sorter at CYTO 2016," PRWeb, Jun. 15, 2016.
Chun H. Chen et al., "Specific Sorting of Single Bacterial Cells with Microfabricated Fluorescence—Activated Cell Sorting and Tyramide Signal Amplification Flourescence in Situ Hybridization," Anal. Chem., 2011, 83, 7269-7275.
Sony Biotechnology, Inc., "Sh00Z Cell Sorter," 2015.
Bio-Rad Laboratories, Inc., "S3e Cell Sorter," 2015.
Becton, Dickinson and Company, "BD FACSJazz," 2013.
Cellector Corporation, Scindo XLR, Technical Specification, 2014.
Cellector Corporation, Scindo XT, Technical Specification, 2014.
Cytonome/ST LLC, Cytonome Viva G1 Cell Sorter, Technical Specifications, 2014.
Miltenyi Biotec GmbH, "MACSQuant Analyzer 10 optical bench," Mar. 2016.
Miltenyi Biotec GmbH, "MACSQuant Instruments," 2014.

* cited by examiner

TEMPORAL MULTIPLEXED EXCITATION FOR MINIATURIZED, PLANAR FLUORESCENCE ACTIVATED CELL SORTING

CROSS-REFERENCE TO RELATED APPLICATIONS

This application claims priority to U.S. Provisional Patent Application No. 62/346,206, filed Jun. 6, 2016, which is incorporated herein by reference.

BACKGROUND

Unless otherwise indicated herein, the materials described in this section are not prior art to the claims in this application and are not admitted to be prior art by inclusion in this section.

Fluorescence activated cell sorting (FACS) is a technique used in cytometry for measuring, sorting and enriching rare cells and particles, such as beads, from large heterogeneous populations. While FACS systems offer desirable multiplexing performance, they can be large and expensive and are typically operated by specially trained staff. As a result, FACS systems are used in only a relatively small number of facilities. To allow for more widespread availability, miniaturized FACS systems (often called "µFACS") have been developed. However, there are few commercial systems to date and those that exist have limited number of both detection and sorting channels compared to traditional FACS.

In one example µFACS system, the laser excitation light shares a common path with the flowing cells. This configuration can limit the microfluidic geometry and involves specialized coatings on the channel to permit optical waveguiding. Such coatings can make the chips more costly to fabricate and may not be suitable for all biological samples. Further, this example system only allows for a single excitation wavelength, which is not desirable if more than about ten fluorescent markers are to be identified. Another example µFACS system offers more channels with up to 4 excitation lasers and 8 fluorescent channels (along with two scatter channels), but employs a cuvette such that the excitation lasers are perpendicular to the collection path. Although this approach may have the advantage that the side scatter channel could be efficiently collected, it may be desirable to use widely available, planar microfluidic chips instead of cuvettes. In addition, this approach uses a large number of detectors, such as photomultiplier tubes (PMTs).

Accordingly, there is a need for systems that are compatible with existing FACS protocols, that are in a planar geometry such as a microfluidic chip, and that can employ a number of simultaneous fluorescent markers and emission channels on the order of what is possible with traditional FACS systems.

SUMMARY

The present invention is directed to µFACS systems and related methods, in particular, µFACS systems having at least two temporally multiplexed excitation lasers.

In one aspect, a system is provided, comprising: (a) at least two excitation lasers; (b) an objective that directs light from the at least two excitation lasers to a common point in an interrogation region of a fluidic channel, wherein the fluidic channel directs a flow of a plurality of fluorescently labeled particles through the interrogation region; (c) at least one modulator that temporally multiplexes light from the at least two excitation lasers such that pulses of light from different lasers intersect the common point in the interrogation region of the fluidic channel at different times; (d) at least one detector; and (e) at least one optical element optically coupled to the objective and the at least one detector to direct light emitted from the plurality of fluorescently labeled particles and transmitted through the objective to the at least one detector.

In another aspect, a method is provided, comprising the steps of: (a) moving a plurality of fluorescently labeled particles through a fluidic channel comprising an interrogation region, wherein the plurality of fluorescently labeled particles move through the interrogation region at a flow speed; (b) directing light from at least two excitation lasers through an objective to a common point in the interrogation region of the fluidic channel; (c) temporally multiplexing light from the at least two excitation lasers such that pulses of light from different lasers intersect the common point in the interrogation region of the fluidic channel at different times; (d) receiving, by at least one detector, light emitted from each of the plurality of fluorescently labeled particles and transmitted through the objective; and (d) generating, by the at least one detector, a fluorescence signal indicative of intensity of light emitted from each of the plurality of fluorescently labeled particles as the particles move through the interrogation region.

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Overview

Flow cytometry is an analytical technique used to measure and analyze the physical and chemical characteristics of individual particles, such as cells, as they flow in a fluid stream through a beam of light. The properties measured can include the relative size, relative granularity or internal complexity, and relative fluorescence intensity of each individual particle. Typically, cell components are fluorescently labelled and then excited by the laser to emit light at various wavelengths. The emitted light is received by one or more detectors, and analyzed, for example, based on how the cell or particle scatters incident laser light and emits fluorescence. FACS is a particular form of flow cytometry that enables a mixture of different particles or cells to be sorted one by one into one or more containers according to their specific light scattering and fluorescence characteristics.

Traditional FACS systems, while being generally commercially available and offering desirable capabilities, can be undesirably large and expensive. Further, while there has been an effort to develop miniaturized FACS systems (often described as μFACS systems), very few commercial μFACS systems currently exist.

In the present disclosure, an example multi-laser μFACS system having two or more temporally multiplexed individual excitation lasers sharing the same optical path is described. With this orientation, the excitation laser spots are coincident on the fluidic channel. The example μFACS system may have a reduced number of detectors, as compared to traditional FACS systems. In some embodiments, the μFACS system is compatible for use with a planar microfluidic chip.

Example μFACS Optical Systems

Figure 1:
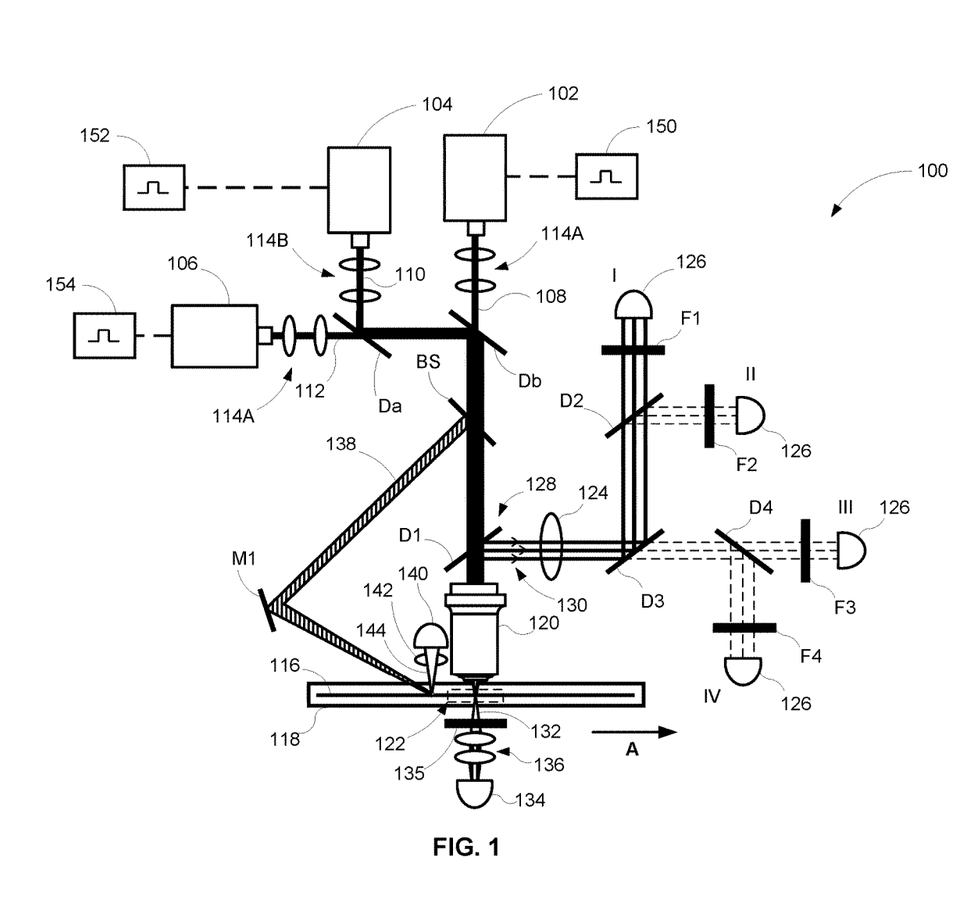
FIG. 1 is a schematic view of an example optical architecture of an embodiment of a µFAC system.

FIG. 1 illustrates a schematic of an example optical architecture of a μFACS system 100 having at least two excitation lasers. In this example, three individual excitation lasers 102, 104, 106 are provided. The use of more than three excitation lasers is contemplated. Light from the excitation lasers 102, 104, 106 is directed through an objective 120 to an interrogation region 122 of a fluidic channel 116. The fluidic channel, which may be defined in a planar microfluidic chip 118, directs a flow of a plurality of fluorescently labeled particles through the interrogation region 122. In the example shown in FIG. 1, the fluidic channel 116 is positioned below the objective 120, such that excitation beams 108, 110, 112 from each of the excitation lasers are incident on the fluidic channel in a plane substantially perpendicular to the direction of fluid flow (A) in the channel.

One or more cylindrical lenses 114A, 114B, 114C may be provided for each laser to shape each of the excitation beams 108, 110, 112 so that the desired beam profile is delivered to the fluidic channel 116 positioned below the microscope objective 120. In flow cytometry applications, it can be desirable to shape the excitation lasers such that they have an elliptical profile and orient the laser spots so that the longer axis of each ellipse is perpendicular to the direction of flow in the fluidic channel.

In this embodiment of system 100, the individual excitation lasers 102, 104, 106 are spectrally multiplexed with dichroics Da, Db such that the beams overlap with each other and share a common optical path through the objective 120. Accordingly, each of the excitation beams 108, 110, 112 is coincident at the same point of the fluidic channel. Modulators 150, 152, 154 are provided for sequentially pulsing the individual drivers 150, 151, 152 such that the pulses from the separate lasers are temporally multiplexed. With this configuration, pulses from each of the lasers 102, 104, 106 will intersect the fluidic channel 116 at the same point, but at different times. In the example shown in FIG. 1, the modulators 150, 152, 154 comprise drivers that modulate the excitation beams 108, 110, 112 by altering the drive current supplied to each of the excitation lasers 102, 104, 106. Alternatively, because some solid-state lasers are not well-suited for direct current modulation, the modulators 150, 152, 154 can be provided as external modulators (not shown), such as gates, for generating the desired pulses.

Figure 2:
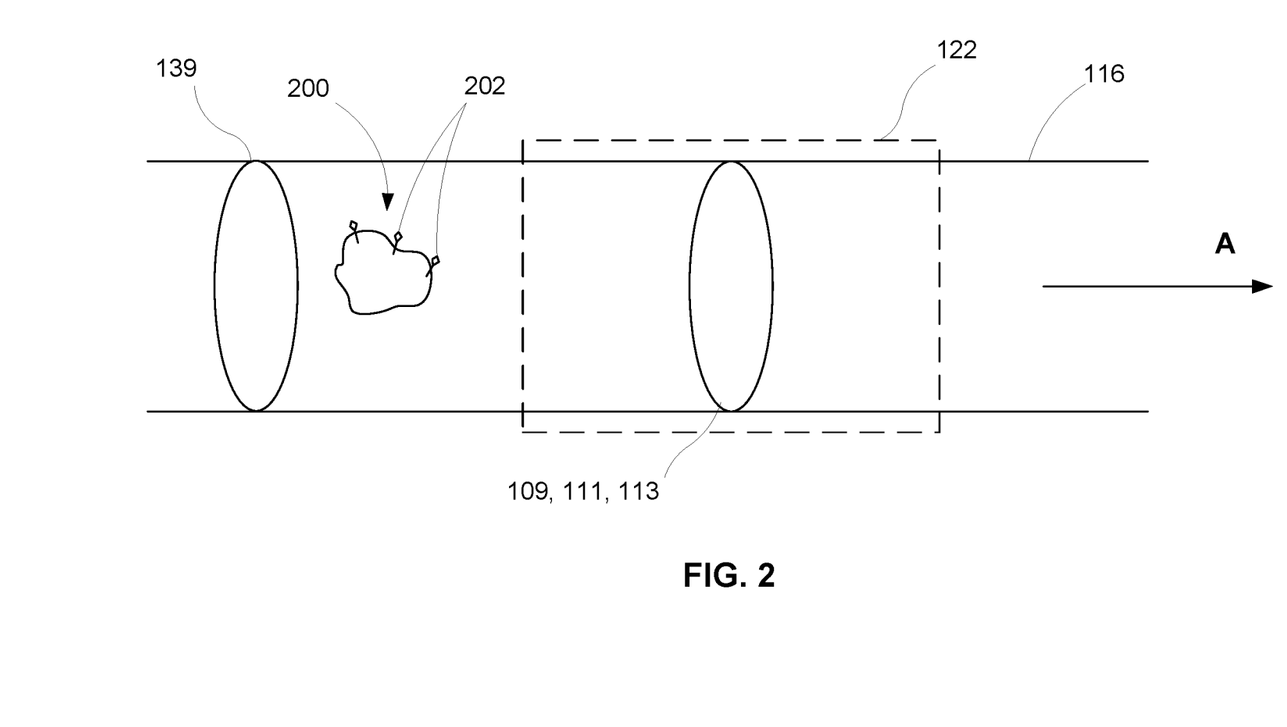
FIG. 2 is a top view of an example interrogation region of a fluidic channel, and illustrating a side scatter beam spot and interrogation beam spot generated by the example µFACS system of FIG. 1.

FIG. 2 is a top view of a portion of μFACS system 100. A sample containing a plurality of fluorescently labelled particles (not shown), such as cells, is introduced into the fluidic channel 116. The system 100 may be designed to detect a plurality of different fluorophores by, for example, using lasers emitting at different wavelengths. For example, different types of particles or cells may each be labelled with different fluorophores, thereby allowing each type of particle or cell to be identified or categorized. The lasers 102, 104, 106 may be selected to emit at a suitable color to excite the fluorophores selected. Individual particle 200, labeled with one or more fluorophores 202, move in the fluidic channel 116 in the direction of fluid flow (A). The fluid flows at a particular flow speed, which may be known and may be manually or automatically controlled. The particle 200 is interrogated as it passes through the coincident laser spots 109, 111, 113 in the interrogation region 122. Also shown is a side scatter beam spot 139, located upstream of the interrogation region 122, with respect to the direction of fluid flow (A), which will be discussed in further detail below.

Fluorescence 130 emitted by each particle as it passes through the coincident laser spots 109, 111, 113 is imaged through the objective 120 and tube lens 124 (if needed) onto one or more detectors 126, such as PMTs, for each of four emission channels I-IV. The amount of fluorescent light emitted can be correlated with the quantity of a particular cell or particle present in the sample. In the example shown in FIG. 1, the fluorescence emission is spectrally separated with a series of dichroics D1, D2, D3 and D4 into the respective emission channels I-IV. Thus, for each emission wavelength, only one single-pixel detector, such as such as a standard PMT, may be provided. By temporally multiplexing the excitation lasers 108, 110, 112, the fluorescence emission 130 associated with each laser will be temporally separated at each of the detectors 126. The fluorescence detectors 126 measure the amplitudes of the fluorescent signals generated by the different fluorescent markers as they move through the interrogation region 122. Numerical values are generated based on pulse heights (amplitudes) measured by each of the various detectors 126. The resulting signals can be input into a processor (not shown) and used to create histograms corresponding to the detected events.

The characteristics of the driving pulse for the excitation lasers 102, 104, 106 can be selected based on one or more factors including, but not limited to, the fluid flow speed, the size of the particles under interrogation, the spot size of each excitation laser on the fluidic channel, the number of emission channels, emission time of the utilized fluorophores, and the response time of detectors 126. The overall period of the pulses (the time it takes to cycle through all of the individual lasers) can be short enough such that the particles being interrogated are equally sampled by each excitation laser. The length of each pulse and the spacing between pulses of each laser can dictate the overall period of the pulses. However, the interval between the individual laser pulses can be long enough to account for the emission time of the fluorophores and the response time of the detectors and the downstream electronics, so that emission generated from each of the excitation lasers is temporally separated at each detector.

In one example, assuming that the maximum flow speed within the fluidic channel 116 is 1000 mm/s and the spot size of an excitation laser is 10 μm wide, a particle will traverse the spot size plane in 10 μs. With four excitation lasers, 2 μs pulses with 500 ns spacing can ensure temporal separation of emission at the detectors. A wider spot size could permit longer pulses, longer spacing between the pulses, or both. In general, the fluorescence lifetime of fluorophores used in FACS is typically on the order of a few nanoseconds, so significant spillage of signal from one temporal slice to another is not likely. Alternately, at the same flow speed, 1 µs pulses could be used to provide oversampling of each particle. In some cases, it may be desirable to excite a particle several times with each laser as it passes through the interrogation space. Further, if the flow speed is known, the temporal multiplexing could be optimized to maximize the collected signal. The order of the lasers could also be optimized so that lasers with minimal spectral overlap are turned on sequentially.

In the illustrated embodiment of system 100, the excitation path shares a common path with the collection path, as they are both coupled through the objective 120. An optical element 128 directs light that is emitted from the plurality of fluorescently labeled particles after it passes through the objective 120 to the detectors 126. In one example, the optical element 128 is provided as a dichroic D1. The dichroic D1 can, in one example, have narrow transmission peaks for the excitation laser wavelengths and reflects all other wavelengths to the fluorescence detectors 126. For simplicity, emission channels II-IV are illustrated with broken lines. Dichroics D2, D3 and D4 direct each emitted fluorescence wavelength to a detector 126 for each respective emission channel. A bandpass filter F1, F2, F3 and F4 may also be provided for each of emission channels I-IV. While FIG. 1 illustrates dichroic D1 transmitting the excitation laser wavelengths and reflecting the emission wavelengths, this could alternatively be switched such that D1 reflects the excitation laser wavelengths and transmits the emission wavelengths. The remaining optics in the system can be reconfigured as necessary.

Alternatively, the optical element 128 may be provided as a dot mirror, in which the excitation laser beams 108, 110, 112 are reflected by small mirrors in a window (called "dot optic"). Since the emitted fluorescence light will occupy the entire back aperture of the objective 120 and a considerable amount of the area of the dot optic, the percentage of emitted light lost in the collection path due to the small mirrors is small. In the three laser system illustrated in FIG. 1, three small mirrors would be required. One possible advantage of this embodiment is that the dot mirror may be less costly to produce and may provide better performance than a multi-band dichroic, such as D1. Alternatively, the optical element 128 may be a dot optic configured to transmit the excitation laser beams 108, 110, 112 through small apertures in a mirror. In either case, because all of the excitation beams are spatially coincident, only a single small mirror or aperture would be needed, regardless of the number of excitation lasers.

In addition to fluorescence emission, forward and side scattered light may also be detected and measured by the system 100 A forward scatter detector 134 and a side scatter detector 140 can generate electrical signals corresponding to detected events as the cells or particles are directed through the fluid channel 116. In one example, shown in FIG. 1, one of the incident laser beams 108, 110, 112 is used for the forward scattering channel. Forward scattered light 132 is scattered through the fluidic channel 116 and is collected by the detector 134. A bandpass filter 135 and one or more tube lenses 136 may also be provided in the optical path.

For side scatter measurements, the same or a different one of the incident laser beams 108, 110, 112 can have its power partially picked off with a beamsplitter BS to provide a side scatter beam 138. A mirror M1 directs the side scatter beam 138 to the fluidic channel 116, and side scattered light 144 is diffusely reflected by particles in the fluidic channel 116. In one implementation (shown in FIG. 1), the side scatter beam 138 is directed to an area of the fluidic channel 116 that is located upstream of the interrogation region 122. In that implementation, the side scattered light 144 is detected by the detector 140 through an optical path that is separate from the objective 120. One or more tube lenses 142 may also be provided in the optical path. In an alternative implementation (not shown), the side scatter beam 138 is directed to the interrogation region 122. In this alternative implementation, the side scattered light 144 is imaged through the objective and detected by the detector 140.

The laser path used for side scatter shown in FIG. 1 (side scatter beam 138 directed to the fluidic channel 116 upstream of the interrogation region 122) could also be used for forward scatter measurements instead of using one of the incident laser beams through the objective 120. One advantage of this alternative architecture is that the system 100 may be able to detect particles more quickly if additional synchronization steps are needed, as both the side and forward scatter measurements are taken prior to the fluorescence interrogation area. In an additional alternative embodiment, side scatter could be measured below the fluidic channel. This configuration may be advantageous as there is more space underneath the channel and it may generate fewer Fresnel reflections.

The objective 120 may also be used in brightfield detection (not shown). This may require an appropriate substitution of the dichroic and an incoherent light source. Brightfield detection may be used to observe the beam spots 109, 111, 113 in the field of view in order to ensure proper alignment of the spots 109, 111, 113 with the fluidic channel 116.

Figure 3A:
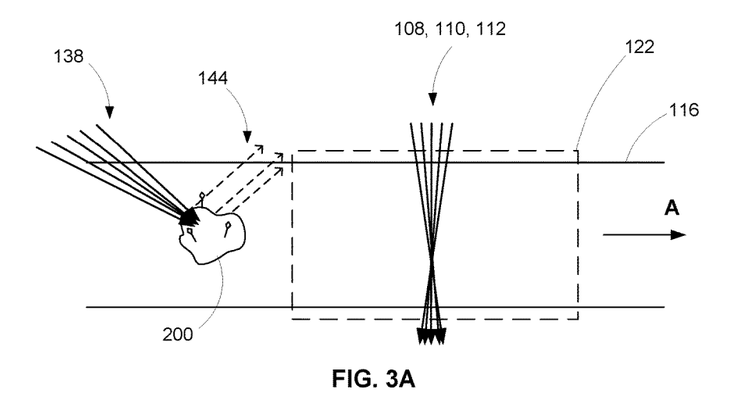
FIG. 3A is a side view of an example interrogation region, illustrating side scatter light generated as a particle passes through a side scatter beam generated by the example µFACS system of FIG. 1.
Figure 3B:
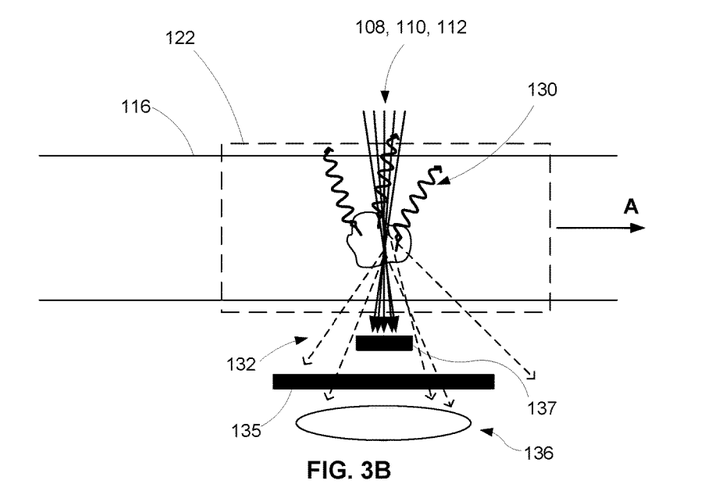
FIG. 3B is a side view of an example interrogation region, illustrating forward scatter and fluorescent light generated as a particle passes through an interrogation light beam generated by the example µFACS system of FIG. 1.

FIG. 3A and FIG. 3B illustrate a side view of a portion of the fluidic channel 116 of the system 100. In the example shown in FIG. 3A, side scattered light 144 is emitted from the fluidic channel 116 when a particle 200 passes through the side scatter beam 138. In the example shown in FIG. 3A, the system 100 is configured such that the side scatter beam 138 intersects the fluidic channel 116 at a position upstream of the position at which the excitation laser beams 108, 110, 112 intersect the channel 116. Alternatively, the side scatter beam 138 could intersect the fluidic channel 116 within the interrogation region 122 so that the side scattered light 144 is imaged through the objective 120.

Forward scattered light 132, in the example shown in FIG. 3B, is transmitted through the fluidic channel 116 when a particle 200 passes through the coincident excitation beams in the interrogation region 122. Fluorescence 130 may be generated, depending on the particular fluorophore(s), as a particle 200 moves through the excitation beams 108, 110, 112.

In order to process the output of the system 100, and ensure that each of the collected signals are assigned to the correct particle in a sample, the side scatter, forward scatter and fluorescence signals from the various laser spots 109, 111, 113 can be synchronized. To do this, the flow speed of the fluid stream in the fluidic channel 116 is determined. In one embodiment, the flow speed of the fluidic channel may be externally controlled, and therefore has a known value. The system 100 may combine each of the scatter and emission signals into a single flow event, provide closed-loop flow speed regulation and precisely synchronize actuation of a deflection system, which is used to sort a particle under interrogation into a capture channel of interest.

The present µFACS system 100 may provide several advantages over existing approaches. First, this approach is compatible with planar microfluidic chips. Second, this approach may allow for a more compact optical setup, while providing as many illumination inputs and outputs as existing FACS systems. Third, this setup may have a simpler method of alignment as all excitation and emission pass through a single element—the objective 120. Fourth, this approach may allow for a more economical detection approach since temporal multiplexing permits the use of a single pixel detector for each emission channel, thereby allowing for more channels with fewer detectors.

Example Method

Figure 4:
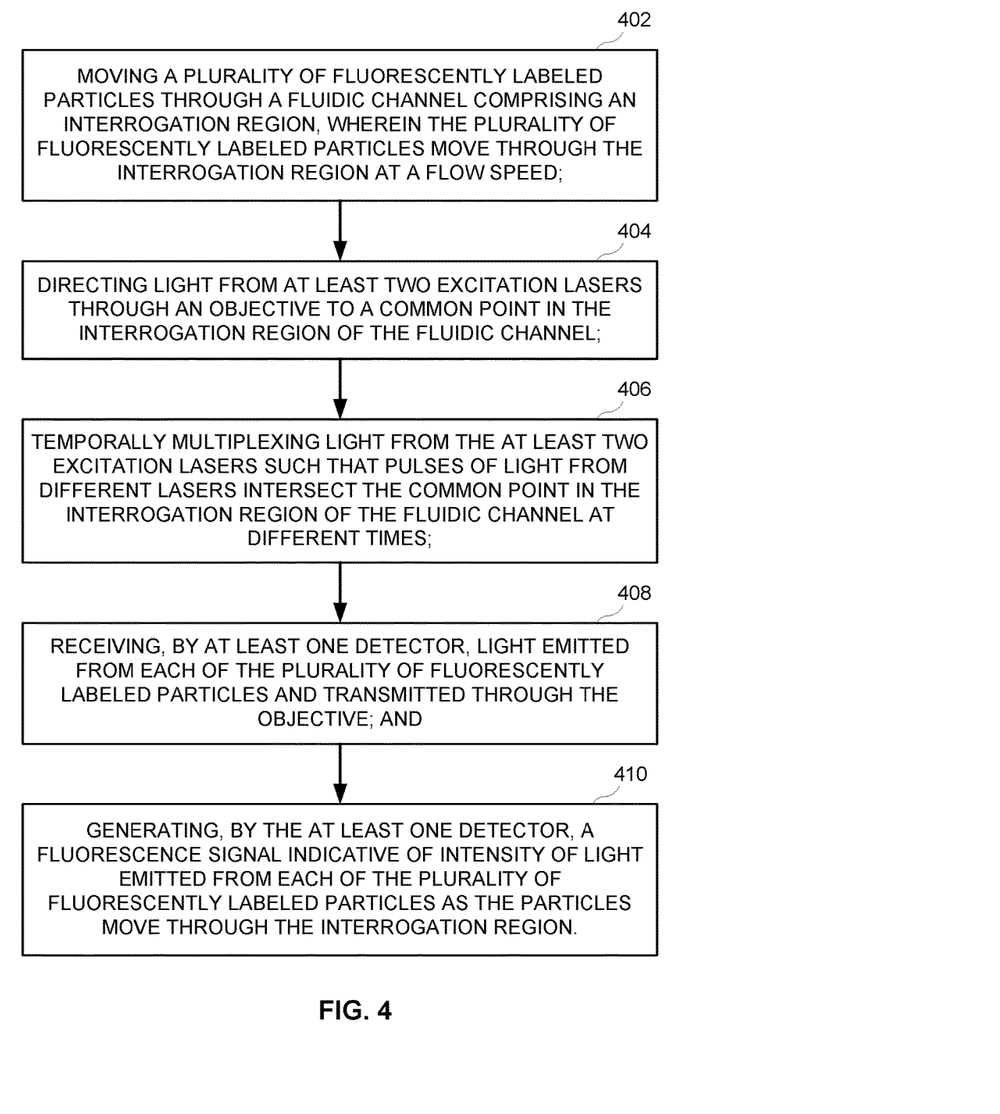
FIG. 4 is a flow chart of an example method.

A flowchart of an example method 400 for operating a µFACS system having at least two lasers to collect one or more of fluorescent, side scatter or forward scatter light, is shown in FIG. 4. In a first step (402), a plurality of fluorescently labeled particles is moved through a fluidic channel, including an interrogation region, of a µFACS system, such as system 100. The plurality of fluorescently labeled particles moves through the interrogation region at a flow speed, which may be known or measured during operation of the system. The plurality of particles may be obtained from a sample source, such as a microtiter plate, by, for example, a probe in fluid communication with the fluidic channel. In some examples, the particles are drawn from the sample source into the fluidic channel by means of a pump, such as a peristaltic pump. The light from at least two excitation lasers is directed through the objective to a common point in the interrogation region of the fluidic channel. (404). Further, the light from the at least two excitation lasers are temporally multiplexed such that pulses of light from different lasers intersect the common point in the interrogation region of the fluidic channel at different times. (406). Light emitted from each of the plurality of fluorescently labeled particles passes through the objective, and is received by at least one detector. (408). The at least one detector generates a fluorescence signal corresponding to the intensity of light emitted from each of the plurality of fluorescently labeled particles, as the particles move through the interrogation region. (410).

The method may also include steps for collecting side and forward scatter light with a µFACS system having at least two lasers, such as system 100. In some examples, a portion of the light from one of the at least two lasers is directed to a location in the fluidic channel for side scatter measurements. The location could be, for example, within the interrogation region or upstream of the interrogation region with respect to the direction of flow in the fluidic channel. At least one side scatter detector receives side scattered light from each of the plurality of fluorescently labeled particles and generates a side scattered signal. The side scattered light is, in some examples, emitted from within the fluidic channel. In some examples, at least one forward scatter detector receives forward scattered light from each of the plurality of fluorescently labeled particles and generates a forward scattered signal. In some examples, the forward scattered light is transmitted through the fluidic channel.

The generated fluorescence, forward scatter, and side scatter signals attributed to a single particle of the plurality of particles can also be synchronized by the system 100. In some examples, the various signals may be synchronized based, at least in part, on the flow speed of the plurality of particles in the fluidic channel. If, for example, the flow speed is known or determined, the system may identify certain events in the fluorescence, forward scatter, and side scatter signals as being attributable to a single particle. The flow speed may be, in some examples, be set and controlled by a pump. Alternatively, the flow speed may be measured or determined.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

The invention claimed is:

1. A system comprising:
    at least two excitation lasers;
    an objective that directs light from the at least two excitation lasers to a common point in an interrogation region of a fluidic channel via a first optical path, wherein the fluidic channel directs a flow of a plurality of fluorescently labeled particles through the interrogation region;
    a beamsplitter that provides a side scatter beam comprising light from one of the at least two excitation lasers, wherein the side scatter beam is directed to the fluidic channel via a second optical path, and wherein the second optical path is different than the first optical path;
    a side scatter detector for detecting side scattered light from particles in the fluidic channel passing through the side scatter beam;
    at least one modulator that temporally multiplexes light from the at least two excitation lasers such that pulses of light from different lasers intersect the common point in the interrogation region of the fluidic channel at different times;
    at least one fluorescence detector; and
    at least one optical element optically coupled to the objective and the at least one fluorescence detector to direct light emitted from the plurality of fluorescently labeled particles and transmitted through the objective to the at least one fluorescence detector.

2. The system of claim 1, wherein the fluidic channel is defined in a planar microfluidic chip.

3. The system of claim 1, wherein the at least one modulator sequentially pulses the at least two excitation lasers.

4. The system of claim 1, wherein the at least one fluorescence detector comprises at least one single pixel detector.

5. The system of claim 1, wherein the at least one fluorescence detector comprises a single pixel detector for each wavelength of light emitted by the plurality of fluorescently-labeled particles.

6. The system of claim 1, wherein the at least one optical element transmits incident light from each of the at least two excitation lasers and reflects light emitted by the plurality of fluorescently-labeled particles.

7. The system of claim 6, wherein the at least one optical element comprises a dichroic having narrow transmission peaks for each wavelength of light incident by the at least two excitation lasers.

8. The system of claim 6, wherein the at least one optical element comprises a dot optic.

9. The system of claim 1, wherein the at least one optical element reflects incident light from each of the at least two excitation lasers and transmits light emitted by the plurality of fluorescently-labeled particles.

10. The system of claim 9, wherein the at least one optical element comprises a dichroic having narrow transmission peaks for each wavelength of light emitted by the plurality of fluorescently-labeled particles.

11. The system of claim 9, wherein the at least one optical element comprises a dot mirror.

12. The system of claim 1, wherein the at least two excitation lasers comprises at least three excitation lasers.

13. The system of claim 1, further comprising a forward scatter detector for detecting forward scattered light transmitted through the fluidic channel.

14. A method comprising:
moving a plurality of fluorescently labeled particles through a fluidic channel comprising an interrogation region, wherein the plurality of fluorescently labeled particles move through the interrogation region at a flow speed;
directing light from at least two excitation lasers through an objective to a common point in the interrogation region of the fluidic channel via a first optical path;
temporally multiplexing light from the at least two excitation lasers such that pulses of light from different lasers intersect the common point in the interrogation region of the fluidic channel at different times;
receiving, by at least one fluorescence detector, light emitted from each of the plurality of fluorescently labeled particles and transmitted through the objective;
generating, by the at least one fluorescence detector, a fluorescence signal indicative of intensity of light emitted from each of the plurality of fluorescently labeled particles as the particles move through the interrogation region;
splitting off a portion of the light from one of the at least two lasers to provide a side scatter beam;
directing the side scatter beam to the fluidic channel via a second optical path, wherein the second optical path is different than the first optical path;
receiving, by at least one side scatter detector, side scattered light from particles in the fluidic channel passing through the side scatter beam; and
generating, by the at least one side scatter detector, a side scattered signal.

15. The method according to claim 14, further comprising:
receiving, by at least one forward scatter detector, forward scattered light from each of the plurality of fluorescently labeled particles; and
generating a forward scatter signal by the at least one forward-scatter detector.

16. The method of claim 15, further comprising:
synchronizing the fluorescence signal, forward scatter signal and side scatter signal attributed to a single particle of the plurality of particles based, at least in part, on the flow speed.

17. The system of claim 1, further comprising:
an optical element that directs the side scatter beam to the fluidic channel at a position upstream of the interrogation region with respect to the direction of flow of the plurality of fluorescently labeled particles in the fluidic channel,
wherein the side scatter detector is positioned to detect side scattered light through an optical path that is separate from the objective.

18. The system of claim 1, further comprising:
an optical element that directs the side scatter beam to the interrogation region of the fluidic channel,
wherein the side scatter detector is positioned to detect side scattered light through the objective.

19. The method of claim 14, wherein the side scatter beam is directed to the fluidic channel at a position upstream of the interrogation region with respect to the direction of flow of the plurality of fluorescently labeled particles in the fluidic channel, and wherein the side scatter detector receives the side scattered light through an optical path that is separate from the objective.

20. The method of claim 14, wherein the side scatter beam is directed to the interrogation region of the fluidic channel, and wherein the side scatter detector receives the side scattered light through the objective.

* * * * *